United States Patent [19]
Herbranson

[11] Patent Number: 5,848,981
[45] Date of Patent: Dec. 15, 1998

[54] METHOD AND APPARATUS FOR HEADACHE RELIEF

[76] Inventor: Larry W. Herbranson, 4310 N. 78th St., Scottsdale, Ariz. 85251

[21] Appl. No.: 656,608

[22] Filed: May 31, 1996

Related U.S. Application Data

[63] Continuation-in-part of Ser. No. 332,899, Nov. 1, 1994, abandoned.

[51] Int. Cl.$^6$ ........................................................ A61F 7/00
[52] U.S. Cl. .......................... 601/134; 601/15; 606/201; 606/204; 606/204.15; 607/108; 607/109; 607/110
[58] Field of Search ..................................... 601/134, 135, 601/15; 606/201, 204, 204.15; 128/898; 607/96, 108, 109, 110, 112

[56] References Cited

U.S. PATENT DOCUMENTS

| | | | |
|---|---|---|---|
| 3,159,160 | 12/1964 | Ullom | 607/109 |
| 4,204,543 | 5/1980 | Henderson | 607/109 |
| 4,776,042 | 10/1988 | Hanson et al. | 2/7 |
| 4,854,319 | 8/1989 | Tobin | 607/109 |
| 4,944,289 | 7/1990 | Matthews | 601/134 |
| 5,119,812 | 6/1992 | Angelo | 607/109 |
| 5,188,103 | 2/1993 | Smith | 12/380 |
| 5,211,623 | 5/1993 | Sarkozi | 602/18 |
| 5,274,865 | 1/1994 | Takehashi | 607/109 |
| 5,295,949 | 3/1994 | Hathaway | 602/18 |

*Primary Examiner*—Richard J. Apley
*Assistant Examiner*—Benjamin K. Koo
*Attorney, Agent, or Firm*—Parsons & Goltry; Robert A. Parsons; Michael W. Goltry

[57] ABSTRACT

A cold pressure apparatus for relieving headache pain including an elongate member constrictively engagable about a head, and a cooling material carried by the elongate member for compressive and cooling engagement with the head.

6 Claims, 3 Drawing Sheets

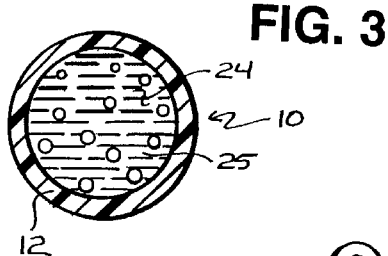
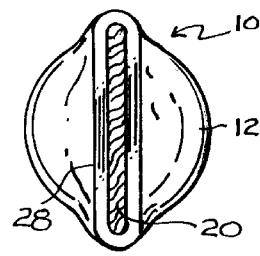
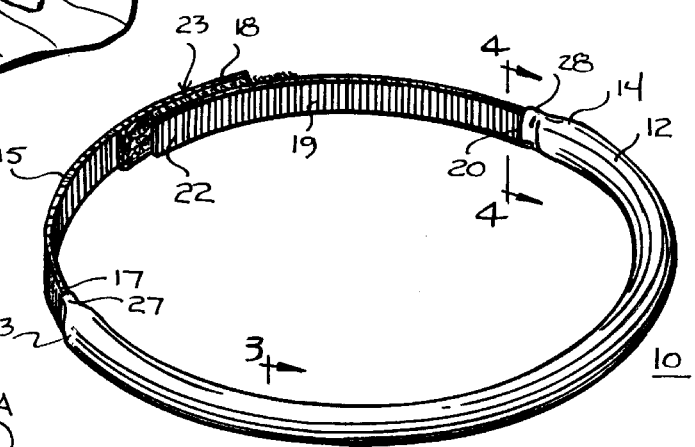
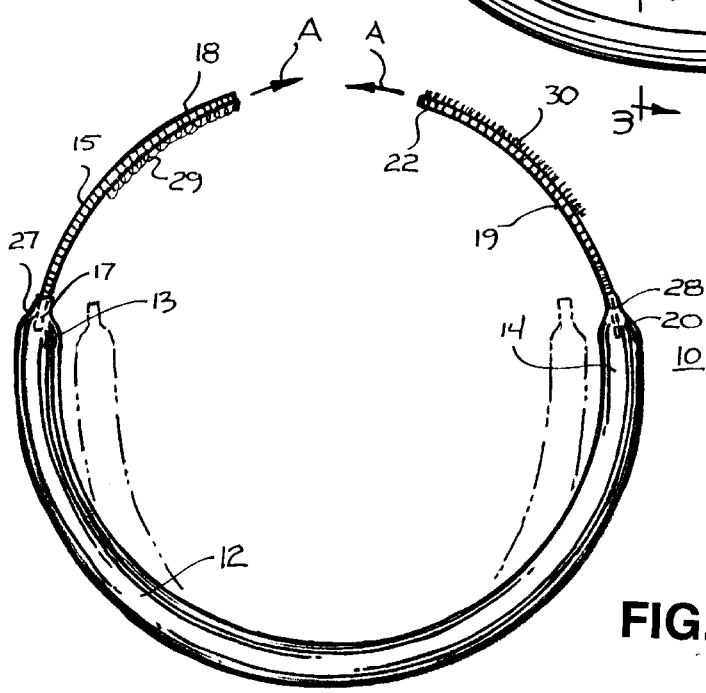

METHOD AND APPARATUS FOR HEADACHE RELIEF

CROSS-REFERENCE TO RELATED APPLICATION

The instant application is a continuation-in-part of applicant's application, Ser. No. 08/332,899, entitled Method and Apparatus for Headache Relief, filed 1 Nov. 1994, now abandoned.

BACKGROUND OF THE INVENTION

1. Field of the Invention

This invention relates to therapeutic devices.

More particularly, this invention relates to headache treatment.

In a further and more specific aspect, the instant invention relates to a device for relieving headache pain.

2. Prior Art

Headaches have always plagued mankind, and can be considered one of the most frequently troublesome symptom. The mechanism of a headache is over stimulation or damage of pain-sensitive structures in or around the head. Some of the pain-sensitive structures are located inside the skull, while others are found in the tissue surrounding the skull. Most headaches result from pain signals generated by tissues surrounding the skull. These headaches are normally referred to as extracranial headaches. The present invention is concerned primarily with relieving the pain generated by extracranial structures. Accordingly, this type of headache will be discussed in greater detail.

The majority of extracranial headaches can be attributed to two sources, dilation and distention of the extracranial arteries supplying blood to the extracranial tissues, also referred to as vascular headaches, and sustained contraction of skeletal muscles of the face, scalp and neck or commonly called tension headaches. Many people suffer from vascular headaches exemplified by migraines. The cause includes dilation and extension of the arteries, the reason for which is not well understood.

Treatment of the vascular and tension headaches vary depending on degree of pain and factors not important to the discussion but generally involve a pharmaceutical treatment. For tension headaches which typically generate low to moderate pain, mild analgesics such as aspirin are quite effective. For more severe head pain stronger pain relievers and muscle relaxants may be used. Each of these has its benefits, risks and side affects. Treatment for vascular headaches may include medication to reduce the dilation of the arteries, pain relievers and muscle relaxants. Again, each may have toxic side effects.

Some ancient techniques for relieving headaches do not employ medication and include acupuncture and acupressure. Efforts have again been directed to developing non-pharmaceutical therapy, but which do not require a high degree of knowledge and experience to use. Specifically, a headband has been developed which employs semi-rigid, pressure inducers. The pressure inducers are supported within a channel of the band and are positionable to engage the head of an individual at specific locations. While somewhat effective in reducing headache pain when properly adjusted, the pressure inducers must be positioned just right to overlie the correct points on the head. Lay individuals would generally not have the specialized knowledge necessary for the correct positioning of the pressure inducers, and therefore the effectiveness of the device would be greatly reduced or eliminated completely.

It would be highly advantageous, therefore, to remedy the foregoing and other deficiencies inherent in the prior art.

Accordingly, it is an object of the present invention to provide an apparatus for relieving headache pain.

Another object of the present invention is to provide a non-pharmaceutical treatment for headaches.

And another object of the present invention is to provide a simple, inexpensive and effective headache relief apparatus.

Still another object of the present invention is to provide a headache treatment which has no toxic side effects.

Yet another object of the instant invention is to provide treatment for headache relief which is easily administered.

Yet still another object of the instant invention is to provide a device which restricts blood flow to the scalp, reducing pain associated with a vascular headache.

And a further object of the invention is to provide a headache relief apparatus which requires no specialized knowledge for use.

Still a further object of the immediate invention is to provide an apparatus which applies cold pressure to the head of an individual suffering from a headache.

And still a further object of the instant invention is to provide an apparatus which incorporates equally spaced-apart substantially linearly aligned permanently substantially rigid pressure inducers positionable about the head of an individual for providing evenly distributed pressure points for comfortably relieving headache pain.

Yet a further object of the instant invention is the provision of constrictively engaging substantially permanently rigid stones or protrusions directly to the head of an individual for relieving headache pain, and without the stones or protrusions occasioning pain to the head of the individual as a result of the direct contact of the permanently rigid stones or protrusions with the head.

SUMMARY OF THE INVENTION

Briefly, to achieve the desired objects of the instant invention in accordance with a preferred embodiment thereof, provided is a cold pressure apparatus for constrictive and cooling engagement with a head. The apparatus includes an elongate member for constrictive engagement with the head, the elongate member having a first end and a second end, fastening means coupled to the first end and the second end for adjustably coupling the first end to the second end, and cooling means carried by the elongate member for compressive and cooling engagement with the head.

In a specific embodiment, the cooling means of the cold pressure apparatus includes a plurality of permanently substantially rigid stones fabricated from cold retaining materials fixed to the elastic material in an equally spaced-apart and linearly aligned configuration by an elastic adhesive. In this embodiment, the elongate member includes an elastic material.

In a further embodiment, the elongate member of the cold pressure apparatus includes a flexible tub having a first end and a second end and the cooling means includes a freezable cooling material carried within the tube. This embodiment also includes fastening means having a first elastic strip coupled to the first end of the tube, a second elastic strip coupled to the second end of the tube, and an engagement pair having an element coupled to one of the first elastic strip and the second elastic strip and a complemental element coupled to the other of the first elastic strip and the second elastic strip. In this embodiment, the flexible tube may include a plurality of linear aligned substantially equally spaced-apart protrusions for engagement with the head, the protrusions being operative for transmitting the coolness to the head provided from the cooling means.

Also provided is a method of treating a headache including the steps of providing a cold pressure apparatus including an elongate member for constrictive engagement with the head, the elongate member having a first end and a second end, fastening means coupled to the first end and the second end for adjustably coupling the first end to the second end, and cooling means carried by the elongate member for compressive and cooling engagement with the head, cooling the cooling means, and securing the cold pressure apparatus about the head of an individual suffering from a headache with the cooling means in compressing and cooling engagement with the head, the cold pressure apparatus restricting blood flow to and cooling the head.

BRIEF DESCRIPTION OF THE DRAWINGS

The foregoing and further and more specific objects and advantages of the instant invention will become readily apparent to those skilled in the art from the following detailed description of preferred embodiments thereof taken in conjunction with the drawings in which:

FIG. 1 is a perspective view of an apparatus constructed in accordance with the teachings of the present invention, as it would appear positioned to reduce an individuals headache pain;

FIG. 2 is a perspective view of the apparatus of FIG. 1 as it would appear in a fastened configuration;

FIG. 3 is a sectional view of the apparatus taken along line 3—3 of FIG. 2;

FIG. 4 is a sectional view of the apparatus taken along line 4—4 of FIG. 2;

FIG. 5 is a top plan view of the apparatus of FIGS. 1–4 as it would appear in an unfastened configuration;

DETAILED DESCRIPTION OF THE PREFERRED EMBODIMENT

Figure 6:
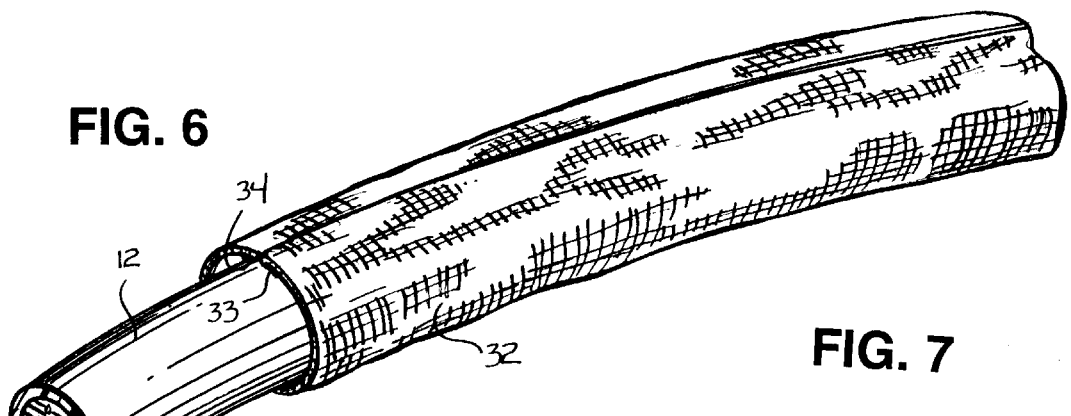
FIG. 6 is an enlarged partial perspective view of the apparatus of FIGS. 1–5 as it would appear with the addition of a cover.

Turning now to the drawings, in which like reference characters indicate corresponding elements throughout the several views, attention is first directed to FIG. 1 which illustrates a first embodiment of the instant invention comprising a cold pressure apparatus 10 positioned about a head of an individual. Cold pressure apparatus 10 is shaped to be worn similarly to a headband, and is adjustable to fit a wide range of head sizes. Cold pressure apparatus 10 is positioned to constrictively encircle the head directly above the ears and horizontal to the eye browns over the lower temple and sinus regions.

Turning to FIG. 2, cold pressure apparatus 10 includes a length of flexible tubing 12 having a predetermined length and diameter, opposing ends 13 and 14, a strip 15 of material preferably elastic in nature, having opposing ends 17 and 18 with end 17 coupled to end 13, a strip 19 of material substantially identical to strip 15, having opposing ends 20 and 22 with end 20 coupled to end 14 and an engagement pair 23 for adjustably coupling ends 18 and 22 of strips 15 and 19 together. Strips 15 and 19 are preferably formed of elastic material to provide cold pressure apparatus 10 with the desired constricting characteristic. With additional reference to FIG. 3, one can see that flexible tubing 12 has a central cavity 24 extending from end 13 to end 14. Central cavity 24 is filled with a freezable cooling material 25, preferably a commercially available material such as Lifoam or Blue Ice, but one skilled in the art will understand that central cavity 24 may be filled with more common materials such as water. Flexible tubing 12 is preferably fabricated from polyvinyl chloride (PVC) although many types of plastic tubing are available and may be used.

End 17 of strip 15 and end 20 of strip 19 are coupled to ends 13 and 14 of flexible tubing 12 respectively, by inserting ends 17 and 20 into the respective ends 13 and 14 of flexible tubing 12. Ends 13 and 14 of flexible tubing 12 are then heat sealed using conventional technology to form joints 27 and 28 securely joining ends 13 and 17, and ends 14 and 20. With additional reference to FIG. 4, an enlarged view of joint 28 is shown. Since joints 27 and 28 are substantially identical only one is illustrated in detail. As can be seen, end 14 of flexible tubing 12 is heated to a malleable state to allow deformation thereof. The sides of end 14 are then compressed and allowed to cool, completely encircling and sealably engaging end 20 of strip 19. Joints 27 and 28 which secure strips 15 and 19 to ends 13 and 14 seal central cavity 24 preventing egress of cooling material 25.

Still referring to FIG. 2, engagement pair 23 consists of an element 29 coupled to strip 15 proximate end 18 and a complemental element 30 coupled to strip 19 proximate end 22. While engagement pair 23 may be any of a wide variety of conventional fasteners such as buckles, snaps, etc., a Velcro® fastener is preferred, with element 29 being the loop material and complemental element 30 being the hook material. One skilled in the art will understand that these may be reversed. FIG. 2 illustrates cold pressure apparatus 10 in a fastened configuration with element 29 engaging complemental element 30. With additional reference to FIG. 5, cold pressure apparatus 10 is illustrated in the unfastened configuration. To fasten strip 15 to strip 19, ends 18 and 22 are moved inward in a direction indicated by arcuate arrowed lines A. The use of the Velcro® fastener makes adjustability simply a matter of overlapping ends 18 and 22 more or less as desired.

In use, cold pressure apparatus 10 is stored in a cooling apparatus such as a refrigerator or freezer until required, or placed in a cooling apparatus to cool or freeze freezable cooling material 25 before use. For increased comfort and effectiveness, cold pressure apparatus 10 is frozen in the fastened configuration to insure that flexible tube 12 is shaped to conform to the head of the individual intending to use cold pressure apparatus 10. Cold pressure apparatus 10 is then positioned on an individual's head as described above, and tightened by stretching elastic strips 15 and 19 before engaging element 29 with complemental element 30 about the head. Cold pressure apparatus 10 will constrict about the head with cooling material 25 in compressive engagement with the head, providing a cold pressure which restricts blood flow to the scalp and thereby reducing or eliminating headache pain.

To provide additional padding, fluid absorption and aesthetic appeal, a sleeve 32 may be used to envelope flexible tubing 12 as shown in FIG. 6. Sleeve 32 may be fabricated by joining opposing edges 33 and 34 of a sheet of material such as cloth fabric. One skilled in the art will understand that there are many conventional manners of joining edges, including but not limited to the use of adhesives, stitching, zippers, fasteners of all kinds and more. Any of these may be used to join edges in the fabrication of sleeve 32. Stitching is illustrated and is preferred.

Figure 7:
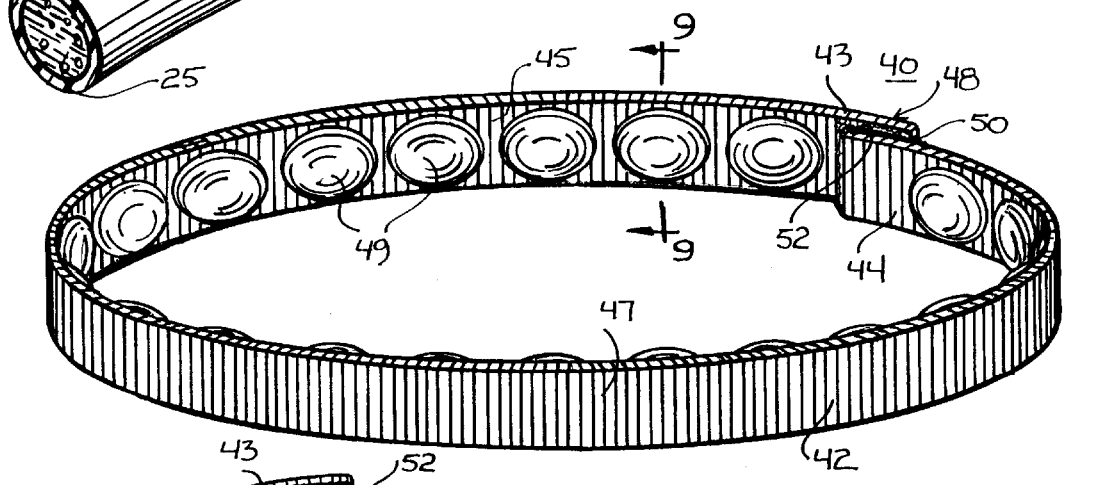
FIG. 7 is a perspective view of another embodiment of the apparatus constructed in accordance with the teachings of the present invention, as it would appear in a fastened configuration.

Another embodiment of a cold pressure apparatus generally designated 40 is illustrated in FIG. 7. Cold pressure apparatus 40 is positioned and used in a manner substantially similar to cold pressure apparatus 10, and includes an elongate member 42 of preferably elastic material having opposing ends 43 and 44, and inner surface 45 and an outer surface 47, an engagement pair 48 for adjustably coupling ends 43 and 44 of elongate member 42 and a cooling material for compressive engagement with the head which, in this embodiment, consists of a plurality of stones 49. Elongate member 42 further includes a predetermined length, width, and height. Engagement pair 48 consists of an element 50 coupled to inner surface 45 proximate end 43 of elongate member 42 and a complemental element 52 coupled to outer surface 47 proximate end 44 of elongate member 42. While engagement pair 48 may be any of a wide variety of conventional fasteners such as buckles, snaps, etc., a Velcro® fastener is preferred, with element 50 being the loop material and complemental element 52 being the hook material. Once skilled in the art will understand that these may be reversed.

Figure 8:
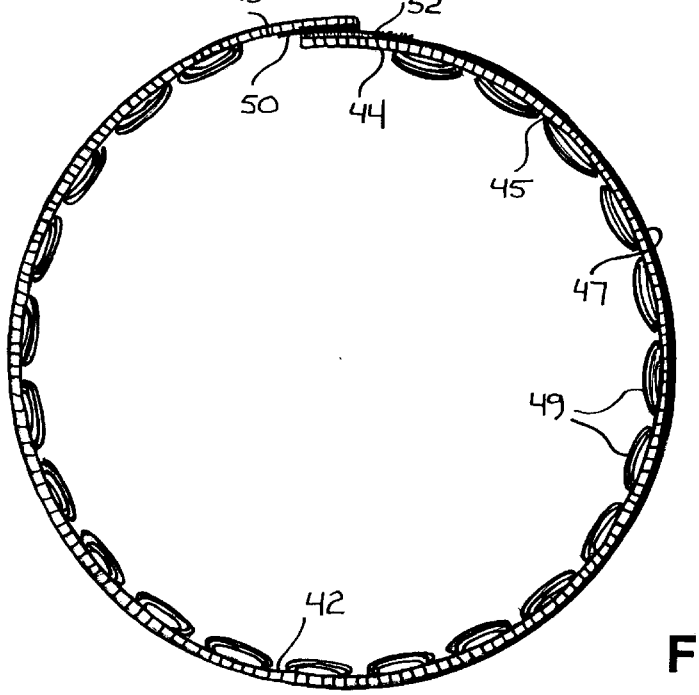
FIG. 8 is a top plan view of the apparatus of FIG. 7.
Figure 9:
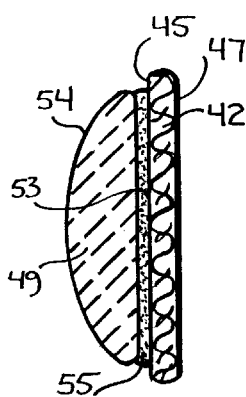
FIG. 9 is a sectional view of the apparatus taken along line 9—9 of FIG. 7.
Figure 10:
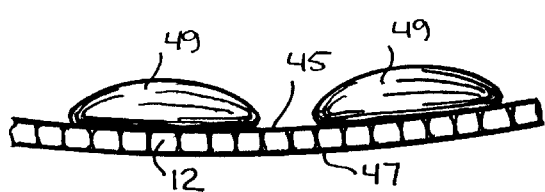
FIG. 10 is an enlarged partial view of the apparatus of FIGS. 7–9, showing the spacing of the pressure stones.

Turning now to FIG. 8, element 50 and complemental element 52 are engaged to form a completed circle configured to constrictively engage an individual's head. Stones 49, being preferably constructed of a permanently substantially rigid or noncompliant material which will retain cold, such as glass, are mounted to inner surface 45 in a spaced-apart preferably linearly aligned configuration so as to press against an individual's head when cold pressure apparatus 40 is in use. With additional reference to FIG. 9, it can be seen that stones 49 are generally hemispherical in shape, having a flattened surface 53 and a convex surface 54. Flattened surface 53 is attached to inner surface 45 in any conventional manner, preferably by bonding with an adhesive 55. An elastic and flexible adhesive such as 6.E silicon is preferred, allowing stretching of the bond between stones 49 and elongate member 42 as elongate member 42 is stretched. Stones 49 are attached to inner surface 45 the entire length of elongate member 42 up to but spaced from element 50 and complemental element 52. Referring to FIG. 10, stones are evenly distributed in linear alignment and preferably evenly spaced apart, or alternatively spaced apart by ¾ to ⅝ inch intervals.

Cold pressure apparatus 40 is used in a manner substantially similar to cold pressure apparatus 10. Cold pressure apparatus 40 is stored in a cooling apparatus such as a refrigerator or freezer until required, or placed in a cooling apparatus to cool stones 49 before use. Because reduced temperature does not significantly effect the flexibility of cold pressure apparatus 40, it is unnecessary to engage element 50 and complemental element 52. Cold pressure apparatus 40 is then positioned on an individual's head as described above, and tightened by stretching elastic elongate member 42 about the head before engaging element 50 with complemental element 52. Cold pressure apparatus 40 will constrict about the head providing a cold pressure where stones 49 contact the head. The pressure and cold from stones 49 restrict blood flow to the scalp and thereby reduce or eliminate headache pain.

From the above discussion, it will be understood that inner surface 45 of elongate member 42 of cold pressure apparatus 40 encompasses an area which in turn encompasses an equal surface area of the head when received about the head. As a consequence, when cold pressure apparatus 40 is received about the head, convex surface 54 (FIG. 9) of stones 49 comprises an engagement surface engageable with the head, with flattened surface 53 (FIG. 9) comprising an non-engagement surface coupled to inner surface 45 of elongate member 42 and having no engagement with the head. Thus, when cold pressure apparatus 40 is received about the head, the engagement surface, herein further defined as a substantially non-compliant contact surface, of stones 49 engages the head for supplying selectively constrictive pressure to the head, and for supplying evenly distributed areas of pressure about the head, with inner surface 45 of elongate member 42 being spaced apart from the head. Additionally, portions of inner surface 45 of elongate member 42 not coupled to stones 49 and not coupled directly to the head comprise a non-contact surface of elongate member 42 within the area of elongate member 42. As such, the contact surface of stones 49 is greater than the non-contact surface of inner surface 45 of elongate member 42 within the area of elongate member 42 encompassed about the head.

Attention is now directed to FIGS. 11–15, which illustrate yet a further embodiment of a cold pressure apparatus being generally designated by the reference character 60. Cold pressure apparatus 60, which in general similarity to the previously described cold pressure apparatus 10 discussed in combination with FIGS. 1–5, includes substantially the same elements. For the purposes of clarity, the specifically referenced common parts will be indicated consistent with those specifically described in combination with cold pressure apparatus 10. However, the instant reference characters will further include a prime symbol, such as for example (reference character)'.

Figure 11:
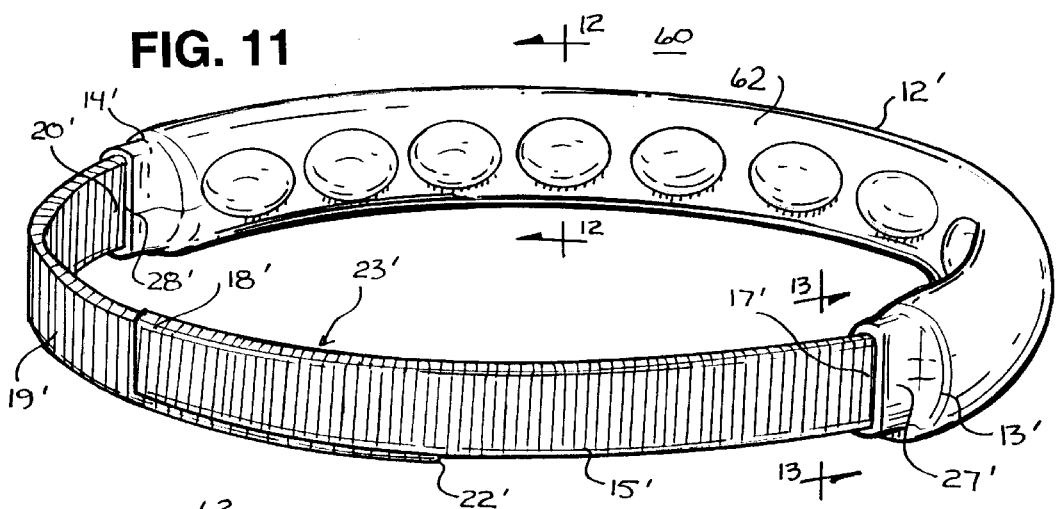
FIG. 11 is a perspective view of yet another alternate embodiment of the apparatus constructed in accordance with the teachings of the present invention, as it would appear in a fastened configuration.

Accordingly, as can be seen in FIG. 11 and like cold pressure apparatus 10, cold pressure apparatus 60 includes a length of flexible tubing 12' having a predetermined length and diameter, an outer surface 62, and opposing ends 13' and 14', a strip 15' of material preferably elastic in nature, having opposing ends 17' and 18' with end 17' coupled to end 13', a strip 19' of material substantially identical to strip 15', having opposing ends 20' and 22' with end 20' coupled to end 14' and an engagement pair 23' for adjustably coupling ends 18' and 22' of strips 15' and 19' together. Strips 15' and 19' are preferably formed of elastic material to provide cold pressure apparatus 60 with the desired constricting characteristic. With additional reference to FIG. 12, one can see that flexible tubing 12' has a central cavity 24' extending from end 13' to end 14'. Central cavity 24' is filled with a freezable cooling material 25', preferably a commercially available material such as Lifoam or Blue Ice, but one skilled in the art will understand that central cavity 24' may be filled with more common materials such as water. Flexible tubing 12' is preferably fabricated from polyvinyl chloride (PVC) although many types of plastic tubing are available and may be used.

Figure 12:
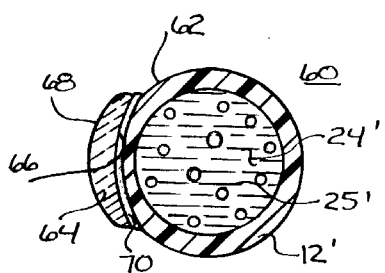
FIG. 12 is a sectional view of the apparatus of FIG. 11 taken along line 12—12 of FIG. 11.
Figure 13:
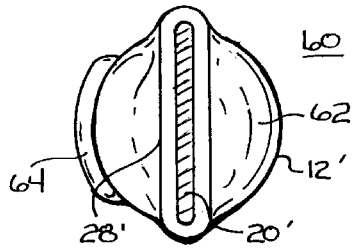
FIG. 13 is a sectional view of the apparatus of FIGS. 11–12 taken along line 13—13 of FIG. 11.
Figure 15:
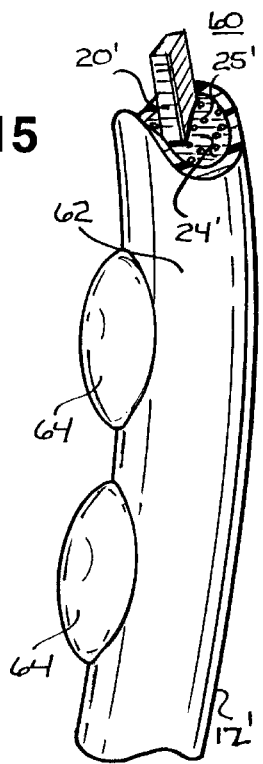
FIG. 15 is an enlarged partial view of the apparatus of FIGS. 11–14, showing the spacing of pressure protrusions.

As can be seen in FIG. 11, further provided are a plurality of protrusions 64, being preferably constructed of a permanently substantially rigid or noncompliant material which will retain cold, such as glass, which are mounted to outer surface 62 in a spaced-apart preferably linearly aligned configuration so as to press against an individual's head when cold pressure apparatus 60 is in use. As can be seen in FIG. 12, it can be seen that protrusions 64 are generally hemispherical in shape, having a substantially concave surface 66 and a convex surface 68. Concave surface 66 is attached to outer surface 62 in any conventional manner, preferably by bonding with an adhesive 70. An elastic and flexible adhesive such as 6.E silicon is preferred. Protrusions 64 are attached to outer surface 62 the entire length flexible tubing 12' up to but spaced from ends 13' and 14'. As can be seen in FIG. 15, protrusions 64 are evenly distributed in linear alignment and preferably spaced apart by ¾ to ⅝ inch intervals. With attention directed to FIG. 13, protrusions 64 may alternatively be integrally molded with flexible tubing 12, and constructed of the same material flexible tubing 12' is constructed.

End 17' of strip 15' and end 20' of strip 19' are coupled to ends 13' and 14' of flexible tubing 12' respectively, by inserting ends 17' and 20' into the respective ends 13' and 14' of flexible tubing 12'. Ends 13' and 14' of flexible tubing 12' are then heat sealed using conventional technology to form joints 27' and 28' securely joining ends 13' and 17', and ends 14' and 20'. With additional reference to FIG. 13, an enlarged view of joint 28' is shown. Since joints 27' and 28' are substantially identical only one is illustrated in detail. As can be seen, end 14' of flexible tubing 12' is heated to a malleable state to allow deformation thereof. The sides of end 14' are then compressed and allowed to cool, completely encircling and sealably engaging end 20' of strip 19'. Joints 27' and 28' which secure strips 15' and 19' to ends 13' and 14' seal central cavity 24' preventing egress of cooling material 25'.

Figure 14:
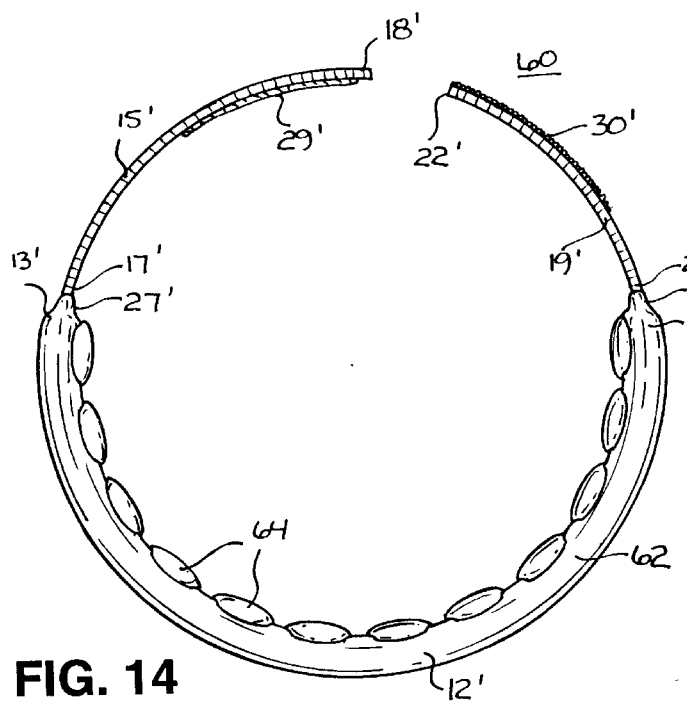
FIG. 14 is a top plan view of the apparatus of FIGS. 11–13 as it would appear in an unfastened configuration.

Referring to FIG. 14, engagement pair 23' consists of an element 29' coupled to strip 15' proximate end 18' and a complemental element 30' coupled to strip 19' proximate end 22'. While engagement pair 23' may be any of a wide variety of conventional fasteners such as buckles, snaps, etc., a Velcro® fastener is preferred, with element 29' being the loop material and complemental element 30' being the hook material. One skilled in the art will understand that these may be reversed. In FIG. 14, cold pressure apparatus 60 is illustrated in the unfastened configuration.

In use, cold pressure apparatus 60 is stored in a cooling apparatus such as a refrigerator or freezer until required, or placed in a cooling apparatus to cool or freeze freezable cooling material 25' before use. For increased comfort and effectiveness, cold pressure apparatus 60 is frozen in the fastened configuration, discussed previously in combination with FIG. 2, to insure that flexible tube 12' is shaped to conform to the head of the individual intending to use cold pressure apparatus 10. Cold pressure apparatus 10 is then positioned on an individual's head as described above, and tightened by stretching elastic strips 15' and 19' before engaging element 29' with complemental element 30' about the head. Cold pressure apparatus 60 will constrict about the head with convex surface 68 of protrusions 64 in compressive engagement with the head, for supplying selectively constrictive and cooling pressure to the head, and for supplying evenly distributed areas of pressure about the head which restricts blood flow to the scalp and thereby reducing or eliminating headache pain.

Various changes and modifications to the embodiment herein chosen for purposes of illustration will readily occur to those skilled in the art. To the extent that such modifications and variations do not depart from the spirit of the invention, they are intended to be included within the scope thereof which is assessed only by a fair interpretation of the following claims.

Having fully described the invention in such clear and concise terms as to enable those skilled in the art to understand and practice the same,

The invention claimed is:

1. An apparatus for relieving headache pain, comprising:

an elongate member constrictively engagable about a head to encircle the head and having an inner surface;

a plurality of permanently substantially rigid elements fabricated from cold retaining materials fixed to said inner surface in substantially linear and evenly spaced-apart relation along substantially the entire length said elongate member, each one of said elements having, a non-engagement surface coupled to said inner surface of said elongate member, and an engagement surface engagable with said head, said engagement surface defining a substantially non-compliant contact surface.

2. The apparatus of claim 1, wherein said elongate member includes an elastic material having a first end and a second end, and a predetermined length.

3. The apparatus of claim 2, further including fastening means coupled to said first end and said second end for adjustably coupling said first end to said second end.

4. The apparatus of claim 3, wherein said permanently substantially rigid stones are fixed to said inner surface by an elastic adhesive.

5. A method of treating a headache comprising the steps of:

providing an an elongate member for constrictive engagement about a head to encircle the head and having an inner surface, a predetermined length and width; and providing a plurality of substantially evenly spaced-apart permanently substantially rigid elements fabricated from cold retaining materials, each of said elements having a non-engagement surface coupled to said inner surface of said elongate member along substantially the entire length of said elongate member, and an engagement surface engagable with said head, said engagement surface defining a substantially non-compliant contact surface; and securing said apparatus member about a head of an individual suffering from a headache with said substantially non-compliant contact surface of said stones in compressing engagement with said head, said apparatus restricting blood flow to said head.

6. The method of claim 5, wherein said step of securing includes:

providing said apparatus further including elastic material having a first end and a second end;

stretching said elastic material for constrictive engagement with said head; and fastening said first end to said second end.

* * * * *